US012797200B2

(12) United States Patent
O'Connor et al.

(10) Patent No.: US 12,797,200 B2
(45) Date of Patent: Nov. 17, 2026

(54) UNICOMPARTMENTAL TIBIAL COMPONENTS

(71) Applicants: ZIMMER GMBH, Zug (CH); John O'Connor, Oxford (GB); Christopher Dodd, Oxford (GB); David Wycliffe Murray, Oxford (GB)

(72) Inventors: John O'Connor, Oxford (GB); Christopher Dodd, Oxford (GB); David Wycliffe Murray, Birmingham (GB)

(*) Notice: Subject to any disclaimer, the term of this patent is extended or adjusted under 35 U.S.C. 154(b) by 498 days.

(21) Appl. No.: 18/271,029

(22) PCT Filed: Jan. 7, 2022

(86) PCT No.: PCT/GB2022/050025
§ 371 (c)(1),
(2) Date: Jul. 5, 2023

(87) PCT Pub. No.: WO2022/148964
PCT Pub. Date: Jul. 14, 2022

(65) Prior Publication Data

US 2024/0050234 A1 Feb. 15, 2024

(30) Foreign Application Priority Data

Jul. 1, 2021 (GB) ..................................... 2100183

(51) Int. Cl.
*A61F 2/38* (2006.01)
*A61B 17/15* (2006.01)
(Continued)

(52) U.S. Cl.
CPC .......... *A61F 2/389* (2013.01); *A61B 17/1764* (2013.01); *A61F 2/30767* (2013.01);
(Continued)

(58) Field of Classification Search
None
See application file for complete search history.

(56) References Cited

U.S. PATENT DOCUMENTS 5,122,144 A 6/1992 Bert et al.
5,207,711 A * 5/1993 Caspari ..................... A61F 2/38 623/20.3
(Continued)

FOREIGN PATENT DOCUMENTS

EP 0709074 A1 5/1996
EP 1550418 A1 7/2005
(Continued)

OTHER PUBLICATIONS

International Search Report and Written Opinion of related international application PCT/GB2022/050025. Mailed Jul. 13, 2022. 26 pages.
(Continued)

*Primary Examiner* — Ann Hu
(74) *Attorney, Agent, or Firm* — Stephen C. Beuerle

(57) ABSTRACT

Unicompartmental tibial components are described herein. A first unicompartmental component (10) comprises a plate (12) having a bearing surface (18) and an opposing surface (22) that is configured to be secured to a proximal end of a patient's tibia, wherein the plate further comprises an anterior end (24), an outer side (25), a posterior end (26) and an inner side (27), wherein a mediolateral width W of the plate is defined between the outer and inner sides, and a longitudinal anteroposterior axis (28) extends between the anterior and posterior ends approximately one third of the width of the plate (i.e. ⅓ W) from the lateral side, and defines a longitudinal axis length L of the plate. A first elongate peg (14) protrudes from the opposing surface in the anterior portion, the first elongate peg defining a first peg axis (32). A second elongate peg (16) protrudes from the opposing
(Continued)

surface in the anterior portion, the second elongate peg defining a second peg axis (34). The first and second peg axes are disposed at an angle of 45-70 degrees with respect to the longitudinal anteroposterior axis and are substantially parallel to one another such that the first and second pegs protrude posteriorly as well as distally with respect to the plate. An anterior portion of the plate comprises a part of the plate defined by an anterior 60% or less of the longitudinal axis length L, whilst a posterior portion of the plate comprises a part of the plate that is defined by the remaining posterior 40% or more of the longitudinal axis length L. The posterior portion of the opposing surface is free from pegs or other fixation devices, and the first and second elongate pegs are located more than half of the mediolateral width W of the plate from an outer edge of the plate. The component is configured for cementless fixation using an interference fit. Also described is a method of installation and a tool suitable for use in installation.

11 Claims, 10 Drawing Sheets

(51) Int. Cl.
*A61B 17/17* (2006.01)
*A61F 2/30* (2006.01)
*A61F 2/46* (2006.01)

(52) U.S. Cl.
CPC ............... *A61F 2002/30004* (2013.01); *A61F 2002/30327* (2013.01); *A61F 2002/30892* (2013.01); *A61F 2002/3093* (2013.01); *A61F 2002/3895* (2013.01)

(56) References Cited

U.S. PATENT DOCUMENTS

| | | | | |
|---|---|---|---|---|
| 7,294,149 | B2 * | 11/2007 | Hozack | A61F 2/389 623/20.34 |
| 8,357,201 | B2 * | 1/2013 | Mayer | A61F 2/30749 623/18.11 |
| 8,632,600 | B2 * | 1/2014 | Zannis | A61F 2/389 623/20.17 |
| 8,690,955 | B2 * | 4/2014 | Rolston | A61F 2/389 623/20.32 |
| 8,758,444 | B2 * | 6/2014 | Wentorf | A61F 2/3886 623/20.32 |
| 8,911,501 | B2 * | 12/2014 | Irwin | A61F 2/38 623/20.32 |
| 9,381,085 | B2 * | 7/2016 | Axelson, Jr. | A61F 2/30771 |
| 9,445,909 | B2 * | 9/2016 | Cohen | A61B 17/1675 |
| 9,700,420 | B2 | 7/2017 | Fitz | |
| 9,937,058 | B2 | 4/2018 | Axelson, Jr. et al. | |
| 10,052,208 | B2 | 8/2018 | Fell | |
| 10,231,840 | B2 | 3/2019 | Servidio | |
| 10,278,827 | B2 * | 5/2019 | Drury | A61F 2/389 |
| 10,456,143 | B2 * | 10/2019 | Justin | A61F 2/30771 |
| 10,456,272 | B2 | 10/2019 | Su | |
| 11,007,064 | B2 * | 5/2021 | Goldberg | A61F 2/4081 |
| 11,540,928 | B2 * | 1/2023 | Schumacher | A61B 17/1615 |
| 11,872,137 | B2 * | 1/2024 | Strohkirch | A61F 2/30771 |
| 2002/0082703 | A1 * | 6/2002 | Repicci | A61F 2/3836 623/20.29 |
| 2005/0125068 | A1 | 6/2005 | Hozack | |
| 2006/0235537 | A1 * | 10/2006 | Kuczynski | A61F 2/38 623/20.36 |
| 2012/0209391 | A1 * | 8/2012 | Cipolletti | A61F 2/389 623/18.11 |
| 2012/0330431 | A1 | 12/2012 | Rolston | |
| 2013/0079669 | A1 | 3/2013 | Stein et al. | |
| 2013/0079672 | A1 | 3/2013 | Stein et al. | |
| 2013/0289731 | A1 * | 10/2013 | Katerberg | A61F 2/389 623/20.32 |
| 2014/0277530 | A1 | 9/2014 | Stalcup et al. | |
| 2017/0333214 | A1 | 11/2017 | Hathaway et al. | |

FOREIGN PATENT DOCUMENTS

| | | | | |
|---|---|---|---|---|
| EP | 1693026 | A1 | 8/2006 | |
| EP | 3254645 | A1 | 12/2017 | |
| FR | 2615726 | A1 | 12/1988 | |
| FR | 2677880 | A1 | 12/1992 | |
| FR | 2738739 | A1 | 3/1997 | |
| FR | 2836821 | A1 * | 9/2003 | A61F 2/38 |
| FR | 2839442 | A1 | 11/2003 | |
| GB | 2388034 | A | 11/2003 | |
| JP | 2010527271 | A * | 8/2010 | A61F 2/3836 |

OTHER PUBLICATIONS

United Kingdom Intellectual Property Office. (UK) Search Report dated Jul. 19, 2021. United Kingdom Application No. GB2100183. 9. English Language. 2 pages.

Communication of Notices of Opposition dated May 27, 2026 in European patent application No. 22700072.6.

Anonymous: "Persona Partial Knee System—Surgical Technique", Surgical Technique, Zimmer Biomet, Jan. 1, 2017 (Jan. 1, 2017), pp. 1-48, XP093399326, Retrieved from the Internet.

Campi S., Mellon S. J., Ridley D., Foulke B., Dodd C. A. F., Pandit H. G., Murray D. W.: "Optimal interference of the tibial componet of the cementless Oxford Unicompartmental Knee Replacement", Bone And Joint Research, British Editorial Society Of Bone And Joint Surgery, vol. 7, No. 3, Mar. 1, 2018 (Mar. 1, 2018), pp. 226-231, XP093399330, ISSN: 2046-3458, DOI: 10.1302/2046-3758.73.bjr-2017-0193.rl.

Mohammad Hasan Raza, Campi Stefano, Murray David, Mellon Stephen: "Instruments to reduce the risk of tibial fracture following cementless unicompartmental knee replacement", The Knee, Elsevier, Amsterdam, NL, vol. 25, No. 6, Dec. 1, 2018 (Dec. 1, 2018), Amsterdam, NL, pp. 988-996, XP093399332, ISSN: 0968-0160, DOI: 10.1046/j.knee.2018.09.001.

Pegg Elise C., Walter Jonathan, D'Lima Darryl D., Fregly Benjamin J., Gill Harinderjit S., Murray David W.: "Journal Pre-proof Minimising tibial fracture after unicompartmental knee replacement: A probabilistic finite element study", Clinial Biomechanics, Elsevier, Amsterdam, NL, Mar. 1, 2020 (Mar. 1, 2020), Amsterdam, NL, pp. 1-34, XP093399338, ISSN: 02689-0033, DOI: 10.1016/j.clinbiomech. 2019.12.014.

* cited by examiner

UNICOMPARTMENTAL TIBIAL COMPONENTS

FIELD OF THE INVENTION

The present invention relates to unicompartmental tibial components, and to methods and devices for the implantation thereof. The invention relates particularly, but not exclusively, to unicompartmental tibial components for cementless implantation.

BACKGROUND TO THE INVENTION

A knee replacement procedure typically involves a surgeon resecting the femur and/or tibia bones of a patient and implanting femoral and/or tibial prosthetic components into the resected bones to replace the articular surfaces thereof. The procedure may be a total knee replacement, in which the articulating surfaces of the femur and tibia (and possibly also the patella) are replaced, or a partial knee replacement in which only some of the articulating surfaces of the knee joint are replaced, such as a unicompartmental knee replacement (also termed a unicondylar knee replacement).

A component that is to be implanted requires some manner of fixation to the resected bone. To this end, tibial components often include one or more anchors, which may be on a base or side of the component, and which are received into cavities created (e.g. drilled, chiselled, burred, sawn) into the patient's bone to help secure the component in place. Such an anchor may be in the form of a keel, which is an elongate protrusion extending from the base of the component generally parallel to an anteroposterior axis of the component.

Bone cement may be used to secure an implant into place (whether the implant is provided with anchors or not). Bone cement can be useful in that it is able to fill any voids between the resected bone and the bottom surface of the implant. However, bone cement can weaken and crack over time, causing loosening and failure of the implant, and/or creating debris within the knee compartment. The bond between the cement and bone can also fail because bone is resorbed. If the component becomes loose it will tend to subside. If a loose tibial component is loaded eccentrically it might lift off as well as subside. For instance, the flexing motion of the knee is known to cause an implant on the tibial plateau to lift off anteriorly, which also may cause failure of the implant and/or produce debris within the knee compartment.

Cementless fixation of unicompartmental knee replacements, particularly medial unicompartmental knee replacements, sometimes achieves better long-term results than cemented. A cementless component is one which is designed to be secured to a resected bone without bone cement. Such components generally comprise a porous or microporous surface to encourage bone ingrowth into the component over time, such ingrowth eventually forming a secure bond between the component and the patient's bone. In order to hold the implant securely in place whilst bone ingrowth occurs, cementless components typically comprise one or more fixation features, such as a keel, which are impacted into a patient's bone to form a press and/or interference fit.

There are two main early complications of cementless tibial fixation, which are tibial plateau fracture and failure of fixation, which will result in loosening and subsidence of the implant, which may be painful for the patient. Although these complications are rare they are major problems for the patients in which they occur.

Tibial plateau fractures usually occur during the first few weeks after implantation. They are probably the result of cracks initiated at operation and propagating thereafter through stressed bone. With cementless fixation the fixation feature, for example a keel, is impacted and has a press fit. The impaction may initiate a crack, and the press fit may generate stress in the bone through which fractures can propagate. Also with a longitudinal keel a slot has to be made in the bone which weakens it. During a unicompartmental knee replacement operation superficial subchondral bone is removed. In the normal knee this bone acts as a tension band preventing the overhanging medial condyle from fracturing off. In the replaced knee the tension band is removed so fractures are more likely to occur.

Tibial component subsidence may take longer to manifest. During common functional activities, with the knee near extension, the load applied to the tibial component is relatively central. As a result, the forces at the bone-implant (or bone-cement) interface below the tibial component are predominantly compressive, which is ideal for cementless fixation. There will also be some shear forces at the interface due to the femoral component moving backwards and forwards during activity. These shear forces will be relatively small (particularly with a mobile bearing when they would be an order of magnitude less than the friction between tibial component and bone). However during activities at high flexion, which are associated with high loads, the force is applied more posteriorly on the tibial component. This tends to cause the component to tilt with the bone posteriorly compressing and the front of the component lifting up off the bone. A common observation on lateral X-rays is an area of radiolucency under the front of cementless components, presumably due to this lift off compromising fixation in this region. When painful subsidence occurs the bone posteriorly collapses and the component slope increases markedly—such a collapse is presumably because the posterior bone is overloaded. Often there is also some associated collapse into valgus, perhaps because the component is better supported on the cortex postero-medially rather than on the relatively soft cancellous bone postero-laterally, and/or perhaps if an associated mobile bearing hits a lateral wall of the component resulting in eccentric lateral loading.

In general the more invasive the method of fixation, the more likely it will be to weaken the bone and thus the more likely it will be to cause a fracture. In addition, forces associated with the interference fit of the components may contribute to fracture. Conversely the less invasive the fixation the less secure the implant will be and the more likely it will be to loosen over time, potentially resulting in bone subsidence or other complications.

US2012/330431 recognises the problem of tibial component anterior lift, and proposes a device for unicompartmental arthroplasty of the knee that comprises a baseplate having a first surface configured to be secured to a surgically prepared medial (or lateral) compartment of a proximal end of a patient's tibia, an opposing second surface configured to replicate a medial (or lateral) tibial condyle, and a flange adjacent the baseplate, the flange shaped to interface with a surgically prepared anterior surface of the proximal end of the patient's tibia. The device further includes at least one anchor protruding from the first surface, the at least one anchor arranged to coincide with at least one corresponding surgically prepared void in the patient's tibia. The flange comprises an orifice therethrough, which permits the introduction of a fastening structure in the form of a rod through the flange and through the patient's tibia towards a receptacle in a posterior of the first surface.

SUMMARY OF THE INVENTION

According to a first aspect of the invention we provide a unicompartmental tibial component comprising:

a plate having a bearing surface and an opposing surface that is configured to be secured to a proximal end of a patient's tibia, wherein the plate further comprises an anterior portion, a posterior portion and a longitudinal anteroposterior axis;

a first elongate peg protruding from the opposing surface in the anterior portion, the first elongate peg defining a first peg axis; and a second elongate peg protruding from the opposing surface in the anterior portion, the second elongate peg defining a second peg axis;

wherein the first and second peg axes are disposed at an angle with respect to the longitudinal anteroposterior axis and are substantially parallel to one another;

wherein the posterior portion of the opposing surface is free from pegs or other fixation devices; and wherein the component is configured for cementless fixation using an interference fit.

The absence of pegs or other fixation devices (such as a keel) in the posterior portion of the component allows for the component to be installed in a manner which reduces trauma to a posterior part of the patient's tibia. The angled nature of the parallel pegs resists removal of the pegs after installation of the component. In particular the angled pegs prevent the front of the component lifting up. (If loaded posterior the component can't move anterior allowing the component to pull straight out). A component having both of these features may be less likely to result in tibial fracture or component loosening after a cementless installation.

Cementless fixation as used herein refers to a component installation method which does not make use of bone cement. A component which is suitable for cementless installation is thus one which can be installed and fixed to a patient's bone without use of bone cement. The components described herein are suited to cementless fixation because the pegs are shaped to form an interference fit with appropriately sized holes formed in a patient's tibia. The components herein do not require any primary fixation other than the interference fit provided by the pegs, and thus no other primary fixation features are provided. The components may additionally comprise a surface structure or treatment on one or more bone-contacting surfaces of the component which encourages bone ingrowth into those surfaces, thus promoting secondary fixation over time.

As referred to herein, the anterior portion of the plate is defined with respect to the longitudinal anteroposterior axis of the plate as being the part of the plate comprising the anterior (front) 60% of that axis or less (e.g. 55% or 50%). The posterior portion is defined as being the remainder of the plate, i.e. that comprising the posterior (rear) 40% of the longitudinal axis or more (e.g. 45% to 50%). The longitudinal anteroposterior axis may be located approximately ⅓ of the width of the plate from an inner edge of the plate, substantially where a keel would be located, if one were present.

The first and second peg axes may be disposed at an angle of 45-70 degrees, or 55-65 degrees, or approximately 60 degrees, with respect to the longitudinal anteroposterior axis. Such obliquely angled pegs may be configured to prevent the component from lifting vertically out of a patient's bone, once implanted. The first and second pegs may be angled towards a posterior of the plate. That is, for each of the first and second pegs, a tip of the peg is located further posterior than a base of that same peg. The pegs may otherwise form an angle of 90 degrees with the opposing surface; that is, the pegs may be angled only in the anteroposterior direction and not in a mediolateral direction.

One or more of the elongate pegs may have a high aspect ratio, for example a ratio of length:width that is 3:2, 2:1, 3:1 or greater. Together with said high aspect ratio, each peg may have a length of 6-12 mm, for example 6, 7, 8, 9, 10, 11 or 12 mm, and a widest diameter of 4-8 mm, for example 4, 5, 6, 7 or 8 mm. Such high aspect pegs reduce the trauma to the tibia, and further reduce the likelihood of the component pulling vertically out of the bone.

A cross section of one or more of the elongate pegs may be elliptical. One or more of the elongate pegs may be tapered. One or more of the elongate pegs may comprise a rounded or tapered tip.

The pegs may be located one behind the other, i.e. the first peg may be located anterior of the second peg. The pegs may be in line with one another (i.e. may fall in the same anteroposterior plane). The plate may comprise an anteroposterior axis length, which may be defined as a length of the longitudinal anteroposterior axis, the first elongate peg (and more specifically the base of said peg, where the peg axis intersects the anteroposterior axis) being located one fifth of the anteroposterior axis length from an anterior end of the axis and the second elongate peg being located half of the anteroposterior axis length from the anterior end of the axis.

The plate may comprise a mediolateral width, which may be defined as a width of the widest part of the plate between an inner side of the plate (i.e. a side intended to be installed closest to the tibial eminence) and an outer side of the plate (i.e. a side intended to be located away from the tibial eminence). Both pegs may be located more than ⅓ of the width from the outer side of the plate, for example, more than ½ of the width from the outer side of the plate, or between ½ and ¾ of the width from the outer side of the plate.

One or more of the elongate pegs may comprise one or more barbs.

The component may comprise a cementless fixation coating on each of the elongate pegs, and the coating may be absent from a region of each peg, such that each said region has a diameter that is narrower than a widest diameter of the coated peg. The coating may be absent from a base region of each peg adjacent the opposing surface, such that each said base region has a diameter that is narrower than a widest diameter of the coated peg.

One or more of the elongate pegs may comprise a region which is narrower than a widest diameter of the peg.

According to a second aspect of the invention we provide a guide tool for a unicompartmental knee procedure, the guide tool comprising:

a guide plate shaped to replicate a plate of a tibial component having a longitudinal anteroposterior axis;

a first drill guide configured to guide a drill through the guide plate along a first drill axis; and a second drill guide configured to guide a drill through the guide plate along a second drill axis;

wherein the first and second drill axes are disposed at an angle with respect to the longitudinal anteroposterior axis and are substantially parallel to one another.

The angle may be 45-70 degrees, for example 55-65 degrees, or approximately 60 degrees.

The guide plate may comprise an anteroposterior length, and the first drill guide may be located one fifth of the length from an anterior end of the guide plate, whilst the second drill guide may be located half of the length from the anterior end of the guide plate.

The guide tool may further comprise a drill stop operable to interact with a drill to prevent the drill from drilling further than a predefined depth through the first or second drill guide.

The guide tool may further comprise a clamp operable to engage between the guide plate and a femur of a patient.

According to a third aspect of the invention, we provide a kit comprising one or more tibial components according to the first aspect of the invention and a guide tool according to the second aspect of the invention. The first drill guide may be shaped (e.g. have a maximum internal diameter sized such that) a hole drilled via the first drill guide has a widest diameter that is narrower than a widest diameter of the first peg. Similarly, the second drill guide may be shaped (e.g. have a maximum internal diameter sized such that) a hole drilled via the second drill guide has a widest diameter that is narrower than a widest diameter of the second peg. The drilled diameter may be, for example, 0.25 mm, 0.5 mm, 0.75 mm, or 1 mm narrower than the corresponding peg diameter.

According to a fourth aspect of the invention we provide a method of fitting a unicompartmental tibial component, the method comprising:

- resecting a surface of a patient's tibia to which the tibial component is to be fitted;
- securing a guide tool in accordance with an embodiment described herein to the resected tibial surface;
- drilling, using a first drill guide of the guide tool, a first oblique peg hole into the resected tibia;
- drilling, using a second drill guide of the guide tool, a second oblique peg hole into the resected tibia, wherein the second peg hole is parallel to the first;
- inserting a unicompartmental tibial component in accordance with an embodiment described herein into the resected and drilled tibia.

The first oblique peg hole may have a widest diameter that is narrower than a widest diameter of the first peg. Similarly, the second oblique peg hole drilled may have a widest diameter that is narrower than a widest diameter of the second peg. The drilled diameter may be, for example, 0.25 mm, 0.5 mm, 0.75 mm, or 1 mm narrower than the corresponding peg diameter.

According to a fifth aspect of the invention we provide a unicompartmental tibial component comprising:

- a plate having a bearing surface and an opposing surface that is configured to be secured to a proximal end of a patient's tibia, and
- a keel protruding from the opposing surface;
- wherein the plate comprises an anterior portion, a posterior portion and a longitudinal anteroposterior axis having an anteroposterior axis length, the anterior portion in this aspect comprising 76% or less of the longitudinal anteroposterior axis length with the posterior portion comprising the remaining 24% or more of the longitudinal anteroposterior axis length;
- wherein the keel lies on the anteroposterior axis and protrudes from the opposing surface in the anterior portion, and wherein the posterior portion of the opposing surface is free from fixation devices, including said keel; and
- wherein the component is configured for cementless fixation using an interference fit.

A typical prior art keel has a length that is approximately 60% or less of the anteroposterior axis length, depending on the size of the component). Such a keel is typically placed centrally on the anteroposterior axis. For example, in the case of a keel having a length that is 58% of the anteroposterior axis, an anterior 21% of the opposing surface would comprise no keel, and a posterior 21% of the opposing surface would also comprise no keel.

In the case of a tibial component according to the fifth aspect of the invention however, the keel is located anteriorly on the plate when compared with conventional keels, and thus causes less damage to the posterior part of the tibia during implantation.

The keel may comprise a leading edge and a trailing edge, the leading edge being located less than 20% (for example 19%, 18%, 17.5%, 17% or less) of the anteroposterior axis length from an anterior rim of the plate and the trailing edge being located more than 23% (for example 24%, 24.5%, 25%, 26% or more) of the anteroposterior axis length from a posterior edge of the plate.

In a conventional keel, a distance d1 between the leading edge and the anterior rim may be equal to a distance d2 between the trailing edge and the posterior rim. In contrast, in the case of the keels described herein, a distance d3 between the leading edge and the anterior rim may be smaller than a distance d4 between the trailing edge and the posterior rim, for example the distance d3 may be 80% of the distance d4, or less, for example 75%, 74%, 73%, 72%, 71% or 70%.

According to a sixth aspect of the invention we provide a unicompartmental tibial component comprising:

- a plate having a bearing surface and an opposing surface that is configured to be secured to a proximal end of a patient's tibia; and
- a keel protruding from the opposing surface;
- wherein the component is configured for cementless fixation using an interference fit; and
- wherein the keel comprises a base portion adjacent the opposing surface, a tip distal from the opposing surface, and medial and lateral side walls, the medial and lateral side walls tapering inwardly from the base portion towards the tip.

That is, the keel is narrower in width (i.e. thinner) towards the tip than it is at the base portion which adjoins the opposing surface. Such a tapering keel allows for a tighter interference fit into the tibia, reducing the likelihood of loosening over time.

The taper angle may be between 0.5-4 degrees, for example 1, 2 or 3 degrees.

According to a seventh aspect of the invention we provide a unicompartmental tibial component comprising:

- a plate having a bearing surface and an opposing surface that is configured to be secured to a proximal end of a patient's tibia; and
- a fixation feature protruding from the opposing surface;
- wherein the component is configured for cementless fixation using an interference fit;
- wherein the component comprises a cementless fixation surface and/or coating on the opposing surface and at least a portion of the fixation feature comprises a smooth outer surface.

The fixation feature may be a keel or a peg, for example an angled peg, such as those described above.

For cementless fixation, the opposing surface and fixation features typically comprise a surface structure or treatment which encourages bone ingrowth into that surface, thus promoting secondary fixation over time. We have noted that rough surfaces, such as those designed for boney ingrowth, can act as a rasp when inserting a cementless component into a prepared tibia. This can widen the prepared holes or slot in the tibia, so reducing the integrity of the interference fit.

In the case of the seventh aspect of the invention such a surface structure or treatment may be partly or fully absent from the fixation feature. Alternatively, a resorbable coating may be provided over part or all of the fixation feature, so as to partly or fully cover any rough surface treatment or coating that is present on the fixation feature.

An insertion surface of the fixation feature may be smooth (e.g. free from any cementless fixation surface and/or coating or covered by a resorbable coating). “Insertion surface” refers herein to a surface of the fixation feature operable to be inserted into a boney cavity first, thus leading the way for the remainder of the fixation feature. The rasp effect of such an insertion surface, if rough, would be significantly higher than any rasp effect due to the remainder of the fixation feature. Thus providing a smooth insertion surface significantly reduces the rasp effect mentioned above. The remainder of the fixation feature may be provided with an (uncoated) surface structure or treatment which encourages bone ingrowth so as to still maintain a large coated surface area for boney ingrowth.

In the case of a peg, the insertion surface may comprise a tip of the peg. The tip of the peg may be smooth, and may be rounded or spherical. A cementless fixation surface and/or coating may be provided on the shaft of the peg. For example, the tip of the peg may have a largest diameter that is wider than the largest diameter of a shaft of the peg, and thus a pocket may be provided between the tip of the peg and the opposing surface, such that a porous coating may be applied to the shaft of the peg between the tip and the opposing surface. The depth of the pocket may be selected such that a coating applied within the pocket does not protrude beyond the largest diameter of the peg tip.

In the case of a keel, the insertion surface may comprise all or part of a posterior (trailing) edge of the keel and all or part of a lower edge of the keel. The insertion surface may additionally comprise all or part of an anterior (leading) edge of the keel. Thus the outer rim of the keel, or a portion thereof, may be smooth. A cementless fixation surface and/or coating may be provided on parts of the keel other than the insertion surface, for example a porous coating may be applied between the smooth outer rim and the opposing surface. A recess or pocket may be provided between the insertion surface of the keel and the opposing surface, such that a porous coating may be provided in the pocket. The depth of the pocket may be selected such that a coating applied within the pocket does not protrude beyond the outer rim in a mediolateral direction.

The entire outer surface of the fixation feature may be smooth. That is, no cementless fixation surface and/or coating may be present on the fixation feature.

A fixation feature may be provided with a surface structure or treatment which encourages bone ingrowth on all outer surfaces, said structure or treatment being fully or partly (e.g. only on an insertion surface, as discussed above) covered by a resorbable coating to provide a smooth surface during implantation. Examples of suitable resorbable materials include calcium paste.

Features of each aspect of the invention may be combined with features from other aspects of the invention if required, as well as with features taken from the description which follows below.

BRIEF DESCRIPTION OF THE DRAWINGS

Reference will now be made, by way of example only, to the accompanying drawings, in which.

DETAILED DESCRIPTION

As explained above, there are two main early complications of cementless fixation, tibial plateau fracture and loosening and painful tibial component subsidence. Contributing factors in these complications are: a) movements at the component-bone interface caused by the loads applied to the tibial component, b) weakening of the bone during component installation, and c) forces within the bone caused by the component being secured via an interference fit, which can cause the bone to split. Such complications can be more prevalent in smaller patients (e.g. those shorter than 5 foot 4 inches). When considering such patients the fixation feature(s) provided on a tibial component can tend to be relatively larger when compared with the size of the patient’s bone than in a taller patient. This can result in relatively more bone needing to be removed in a smaller patient than in a larger patient, thus leaving the remaining bone relatively weaker, and more prone to fracture or subsidence.

Figure 1:
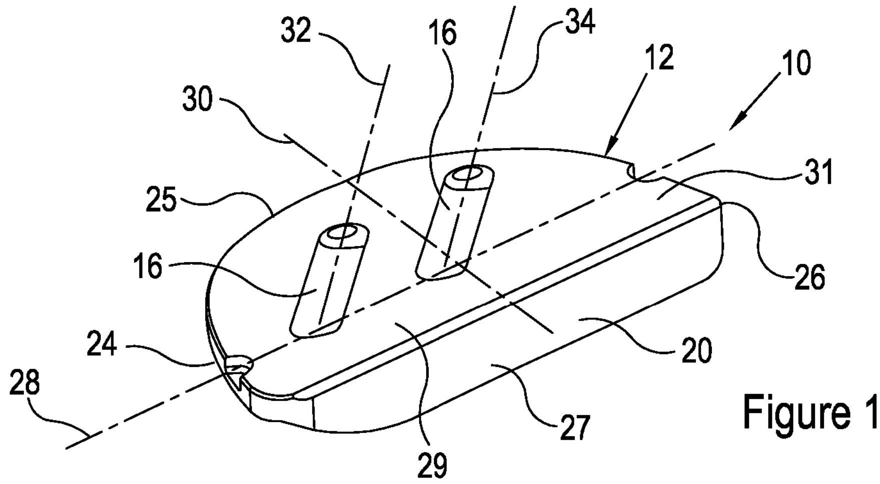
FIG. 1 shows a perspective view of an underside of a tibial component.
Figure 2:
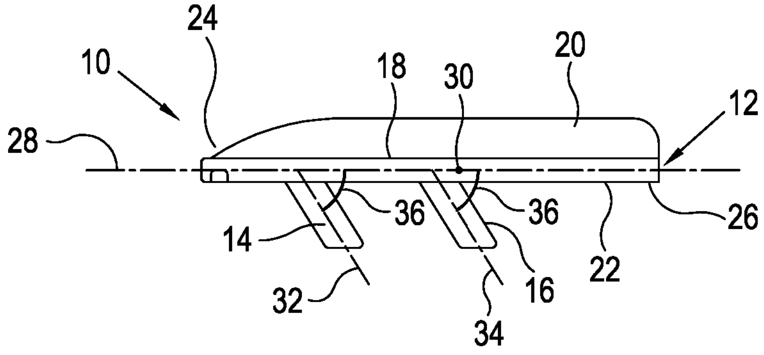
FIG. 2 shows a side view of the tibial component of FIG. 1.
Figure 3:
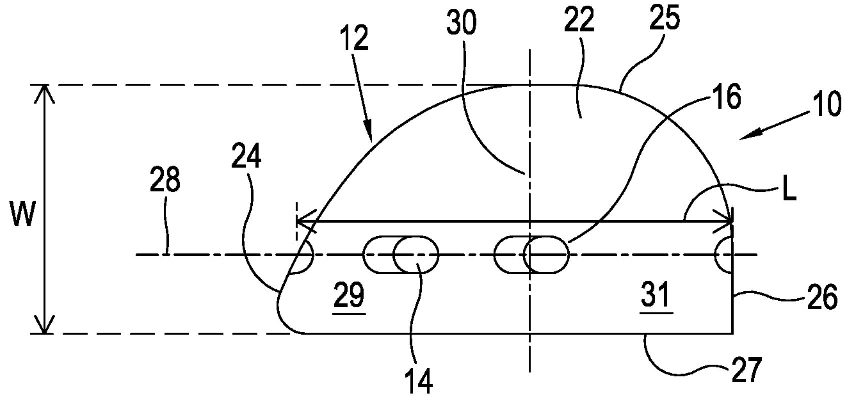
FIG. 3 shows a plan view of the underside of the tibial component of FIG. 1.
Figure 4:
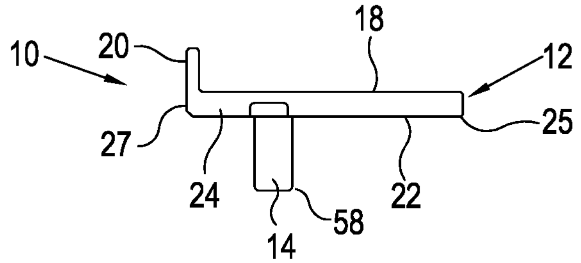
FIG. 4 shows an anterior view of the tibial component of FIG. 1.

FIGS. 1-4 show a tibial component 10 for use in a unicompartmental knee replacement procedure. The component may be for a medial or lateral compartment of a patient’s knee. In the example shown the component is shaped to fit a medial compartment. In FIGS. 1 and 3, the component is shown with its bone/component interface uppermost. In FIGS. 2 and 4, the component is shown with its bearing surface 18 uppermost.

The tibial component 10 includes a plate 12, and at least one elongate peg. In the example shown there are two elongate pegs, a first peg 14 and a second peg 16. It will be appreciated that more elongate pegs could be provided if required, for example three, four or five pegs, or more.

The plate 12 is configured to replace an articular surface of the patient's tibia, in this case a medial tibial bearing surface. The plate includes a bearing surface 18, which when installed will take the place of the patient's tibial bearing surface. The bearing surface 18 is thus shaped to cooperate either directly with a patient's femur (or a femoral replacement component) or with a bearing component located between the tibial component and the femur/femoral replacement component.

The plate 12 is, in the example shown, substantially flat, and has an outline shaped to mimic the natural shape of the head of a patient's tibia. The example shown is a medial tibial component, and hence the plate is generally C-shaped on a medial side, and comprises an upstanding wall or lip 20 on an opposing lateral side that is intended to abut a central tibial eminence of the patient's tibia, when the component is installed. A lateral tibial component would be a mirror image of the component that is shown. It will be appreciated that the plate could have a different shape, and may for instance be generally rounded or elliptical.

An opposing surface 22 of the plate is configured to be secured to a proximal end of a patient's tibia, as will be discussed in more detail later.

The plate 12 has an anterior end 24, a medial side 25, a posterior end 26 and a lateral side 27. A mediolateral width W of the plate is defined between the medial and lateral sides, and a longitudinal anteroposterior axis 28 extends between the anterior and posterior ends approximately one third of the width of the plate (i.e. ⅓W) from the lateral side, and defines a longitudinal axis length L of the plate. It will be understood that the longitudinal anteroposterior axis 28 typically lies in the plane of the plate. Thus, where the opposing surface is flat, the longitudinal anteroposterior axis 28 typically lies in the plane of the opposing surface 22.

Primary fixation is essential to hold the component still after implantation, so as to allow the bone to grow into and stick to the implant and achieve secondary fixation. As explained above, a common mode of loosening is posterior subsidence/anterior lift off, and thus the anterior part of the component should be held down. We have found that in order to minimise the risk of subsidence in the bone at the posterior of the tibia, as much of the posterior part of the tibial surface as possible should be left intact with no holes for fixation.

To this end it is useful to consider the plate 12 as comprising a hypothetical line 30 dividing the plate mediolaterally into an anterior portion 29 and a posterior portion 31. In the example shown, the anterior portion comprises a part of the plate defined by an anterior 50% of the longitudinal axis length L (also termed herein the anterior 50% of the plate), whilst the posterior portion comprises a part of the plate that is defined by a posterior 50% of the longitudinal axis length L (i.e. the remainder of the plate, also termed herein the posterior 50% of the plate).

The line 30 thus divides the longitudinal axis 28 in half in the example shown. It will be appreciated that the dividing line 30 may divide the longitudinal axis differently, for example, the anterior portion could be defined as the anterior 60% of the plate, with the posterior part then being the remaining (posterior) 40% of the plate. The anterior:posterior ratio between the anterior part of the plate and the posterior part of the plate may be 60:40 or less, e.g. 55:45 or 50:50. The posterior portion thus comprises at least 40% of the plate, as defined according to the longitudinal axis length, as discussed above.

The plate 12 is provided with at least one elongate peg, 14, 16 protruding from the opposing surface 22 in the anterior portion 29 of the component. The posterior portion 31 of the component is free from pegs or other fixation features. More specifically, the base(s) of said elongate peg(s) are located in the anterior portion and not in the posterior portion (since the shaft of at least the most posterior of the pegs may extend over the hypothetical dividing line 30). The component does not comprise a keel, and does not comprise any additional primary fixation features other than the legs 14, 16.

The peg or pegs 14, 16 are configured to hold the component still to allow bone ingrowth into the component over time. In particular, the pegs 14, 16 are configured to form an interference or press fit with holes drilled into a patient's tibia.

In the example shown the plate 12 includes two pegs, a first elongate peg 14 and a second elongate peg 16. Both pegs 14, 16 are located in the anterior portion 29 of the plate. In the example shown, the first elongate peg is spaced between the second peg 16 and the anterior end 24 of the plate. However, it will be appreciated that other peg configurations are possible. For instance, the pegs could both be located at the same longitudinal position and spaced apart mediolaterally, or the pegs could be spaced at different longitudinal and mediolateral positions. In no configuration, however, are any pegs (or other fixation features) located in the posterior portion 31 of the plate. Further, no pegs are located adjacent an outer edge (in this case the medial edge) of the plate, so as to avoid weakening the shallower bone in that area. In the example shown, the outer two thirds of the plate (i.e. ⅔W) are free of pegs. In other examples the outer half, or outer third, may be free of pegs.

In the example shown, the second peg 16 is located substantially on the dividing line 30, such that the dividing line 30 passes through the peg base. One possible configuration is thus to locate the first peg 14 about one fifth (20%) of the longitudinal axis length and to locate the second elongate peg about half of the longitudinal axis length.

The first elongate peg 14 defines a first peg axis 32 (i.e. an axis longitudinal to the peg itself), and the second elongate peg defines a second peg axis 34. Both peg axes are disposed at an angle 36 with respect to the longitudinal anteroposterior axis of the plate. "An angle" as used above means an acute angle significantly less than 90 degrees, such that the pegs are oblique with respect to the plate, such that the pegs extend posteriorly as well as distally with respect to the plate. The angle may be between 45-70 degrees, for example between 55-65 degrees, and in the example shown is around 60 degrees. Both pegs are disposed at the same angle, such that the pegs are substantially parallel to one another. It will be understood that "the angle" here refers to an angle in the antero-posterior direction. That is, the pegs are not angled in a mediolateral direction.

It will be seen that posterior to the second elongate peg 16 the opposing surface 22 of the plate is free from pegs or other fixation devices, so minimising the trauma to the posterior of the bone during installation as much as is possible.

When sufficiently loosened a cementless component can pull out of the bone into which it is fitted. However, except in cases of fracture, such components are only able to pull out of the bone in a direction parallel to the fixation pegs. The oblique nature of the anterior pegs 14, 16 ensures that the pegs are configured to resist the component pulling vertically out of the bone, and hence to resist front of the component being lifted up when there is posterior loading with the knee in flexion.

The parallel nature of the pegs makes the component ideal for cementless fixation, as the component can be pushed into place to form an interference fit within appropriately drilled holes located in the resected tibial surface. For a secure interference fit, the drilled holes should have a narrower diameter than the diameter of the pegs that they are intended to mate with, for example 0.5 mm narrower, or 1 mm narrower.

Both pegs, in the example shown, are located in line with one another (i.e. in line with an axis that is parallel to the longitudinal axis). They are disposed on an inner (in this case, lateral) side of the plate (i.e. closer to the lip 20 than to the curved outer edge—in this example about one third of the plate width from the lip, substantially on the longitudinal axis 28). This ensures that the pegs are configured to be installed into the deeper bone closer to the centre of the tibia, rather than into the overhanging bone towards the edge of the compartment that is being resurfaced.

One or more of the elongate pegs, and in this case both pegs 14, 16, has a high aspect ratio. That is, the pegs are narrower than they are long. The ratio of length to width may be 3:2, 2:1 or greater. A high aspect ratio configures the pegs to penetrate deep into the bone, which can prevent the bone above the lower part of the peg lifting up or breaking off. With narrow pegs little bone needs to be removed in the upper part of the tibia, leaving a large amount to transmit tension and prevent fracture. A sufficiently high aspect ratio may be achieved by pegs having a length of 6-12 mm and a widest diameter of 4-8 mm. In the example shown the pegs are approximately 9 mm long and 5 mm at their widest diameter. Pegs for cemented implants typically have a much lower aspect ratio, and are often as wide as they are long. This requires larger cavities to be formed in the bone, weakening the patient's tibia.

The cross section of one or more of the elongate pegs, and in this case the cross section of both pegs 14 and 16, may be elliptical. In particular, the pegs may be narrower in an anteroposterior direction than in a mediolateral direction. This further reduces the amount of bone which needs to be removed from the tibia in order to achieve secure fixation of the component. In addition, a wider mediolateral dimension would further resist anterior lift off.

The component shown is configured for cementless fixation. That is, the component preferably comprises a cementless fixation surface on the opposing surface, and an exterior of the wall 20. Such a coating may also be provided on one or more of the elongate pegs. Such a surface could be a porous or microporous coating, with or without an active surface such as hydroxyapatite.

It will be appreciated that the component shown in FIGS. 1-4 is an example only, and other designs are possible. Some exemplary alternative designs are shown in FIGS. 5*a*-5*e*. Like reference numerals are used for like features, and it will be understood that features discussed above with respect to the component shown in FIGS. 1-4, although not discussed below, may nevertheless be present in the components of FIGS. 5*a*-5*e*.

Figure 5A:
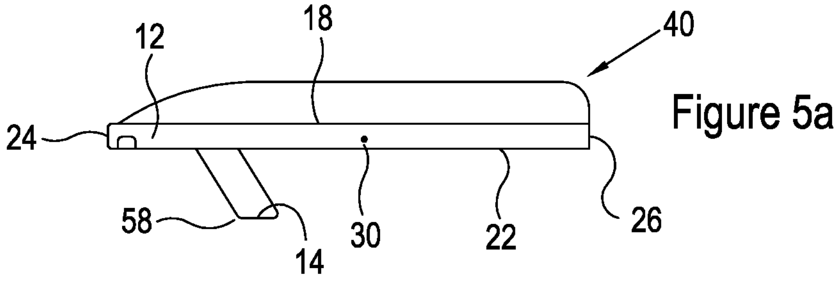
FIGS. 5*a*-5*e* each show a side view of an alternative tibial component.

FIG. 5*a* shows a tibial component 40 that includes a plate 12, similar to the plate discussed above. The component includes only a single fixation peg 14 located in an anterior portion 29 of the plate. The opposing surface of the plate that is posterior to the elongate fixation peg 14 is entirely free of pegs and other fixation devices. The single fixation peg is, in the example shown, located approximately one fifth of the longitudinal axis length of the component. It will be appreciated that other locations are possible, e.g., one quarter or one third of the longitudinal axis length of the component.

Figure 5B:
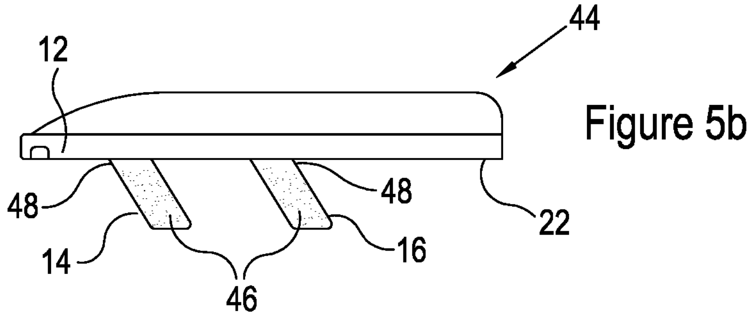

FIG. 5*b* shows a tibial component 44 that includes two elongate oblique pegs 14, 16, similar to the component shown in FIGS. 1-4. The pegs 14, 16 of the component 44 are coated with a cementless fixation coating 46, such as a porous or microporous coating, with or without an active surface such as hydroxyapatite. The coating is not provided (i.e. is absent from) a region 48 of each peg, which in this example is a base region that is adjacent the opposing surface 22.

In the example shown, the fixation coating is applied to the majority of the surface of the peg, but is not applied in a base region extending 1-2 mm below the opposing surface 22 of the tibial component.

Coating could be omitted for example by masking a portion of the peg, such as a base portion 48, when the porous costing is applied. This has the effect that the masked region of the peg has a diameter that is narrower than a widest diameter of the coated portion of the peg. The porous coating (with or without hydroxyapatite) may be about 0.35-0.4 mm thick. Omission of such a coating in a region of a peg would thus result in a narrowed region that is about 0.7-0.8 mm less in diameter than the remainder of the peg. This narrowed region may still be coated in hydroxyapatite.

Figure 5C:
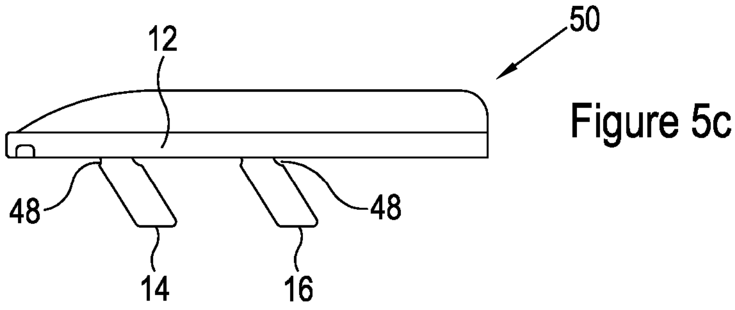

Providing a narrower region of each fixation peg could make the peg less likely to pull out once fitted. A narrower region at the base of each peg could also reduce the likelihood of the rim of bone breaking off. FIG. 5*c* shows an alternative example of a tibial component 50 having a pair of elongate pegs 14, 16, each provided with a base region 48 adjacent the opposing surface which is narrower than a widest diameter of the peg. Such a narrower region may be created as described above (by omitting a coating in this region) or by another method such as by crimping or otherwise compressing the peg after a coating has been applied.

Figure 5D:
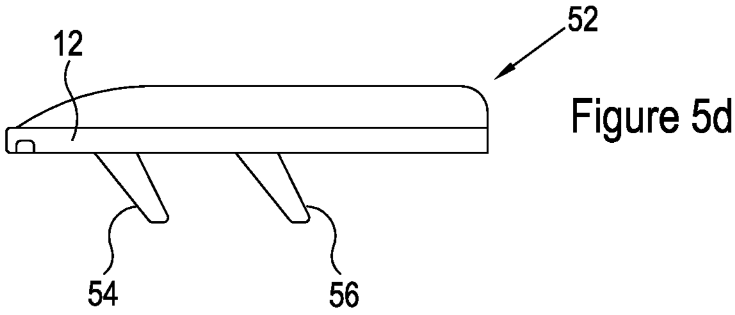

FIG. 5*d* shows a further alternative example of a tibial component 52 having a pair of elongate pegs 54, 56, each of which is tapered. Although the pegs may be parallel sided, as shown in connection with the components of FIGS. 1-5*c*, the peg or pegs alternatively may have a slight taper, for example of a few degrees, as shown in FIG. 5*d*. Such a taper could make it easier to insert the peg and/or could potentially enhance the fixation. The entirety of the peg of pegs need not be tapered. Alternatively, only a tip of the peg may be tapered. This would also aid insertion.

The components of FIGS. 1-5*c* all show components having a peg or pegs including a rounded tip 58, in particular a flattened end with rounded edges, which maximises fixation area. The component 60 shown in FIG. 5*e* differs in that each of the pegs is provided with spherical end 62. Again, this could aid insertion.

Figure 5E:
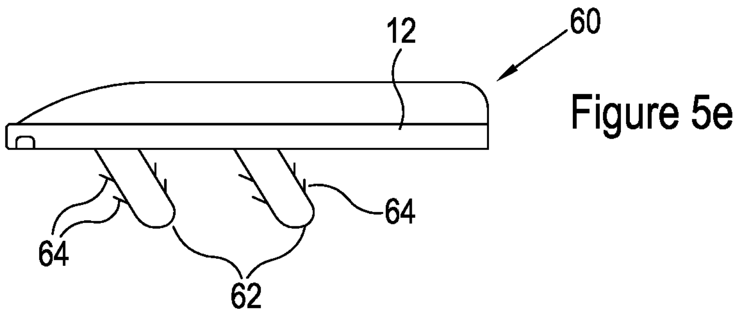

The component shown in FIG. 5*e* is additionally provided with one or more barbs 64, configured to resist the removal of the component after installation. Alternatively, a circumferential barb could be formed by omitting or crimping a region of the porous coating on the peg, or by machining.

The components described herein may be made from any suitable strong and bio-inert material, such as cobalt chrome or titanium alloy. Any porous coating operable to permit or encourage bone ingrowth may be applied to the bone-contacting surfaces of the component, such as plasma sprayed titanium or tantalum.

Figure 6:
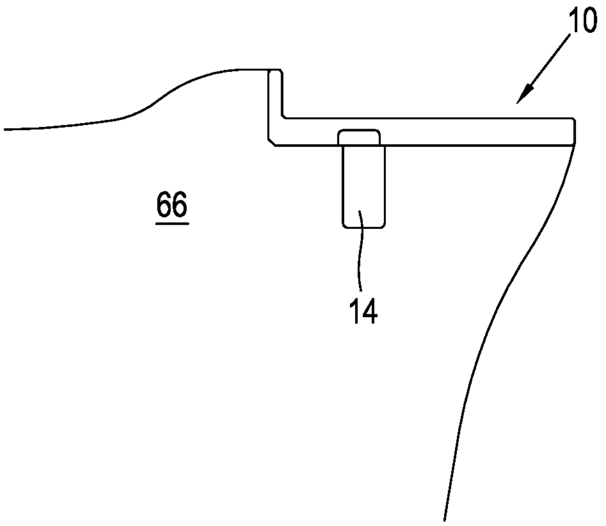
FIG. 6 schematically shows an anterior view of the tibial component of FIG. 1 when implanted into a tibia FIG. 7 schematically shows a lateral view of the tibial component of FIG. 6.
Figure 7:
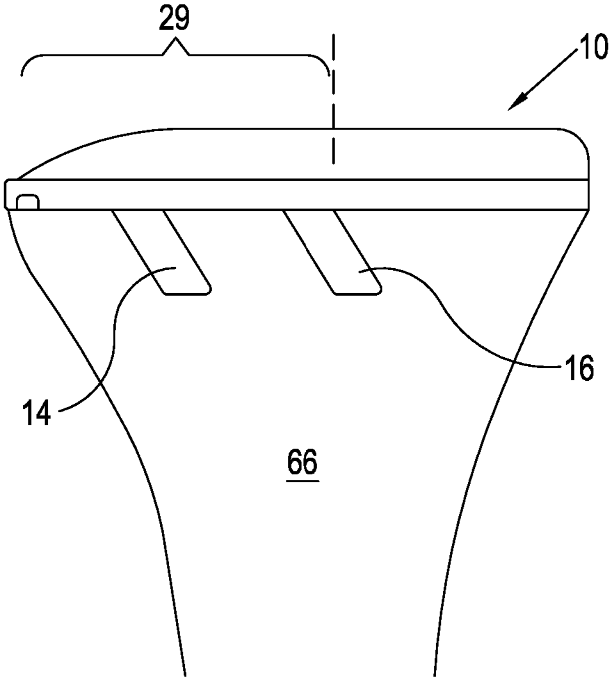

FIGS. 6 and 7 show, respectively, an anterior view and a lateral view of the tibial component 10 installed in a patient's tibia 66. As discussed above, an oblique peg, and in this case two oblique pegs 14, 16, positioned anteriorly in the tibia are used to provide fixation for the tibial component. The pegs are oblique, predominantly in the anteroposterior plane of the component, and slope distally and posteriorly (down and back). The anterior positioning of the pegs on the tibia and their inclination to the vertical leaves enough space for them to be driven into the tibia even in the presence of the femur 104, with all the ligaments resisting distraction of the joint.

Such a component may be installed using cement, but is ideal for a cementless installation. In a cementless component (i.e. a component provided with a cementless fixation surface) one or more holes slightly narrower than the peg(s) should be drilled in an appropriate place into a resected tibia, and the peg(s) forced into the hole to provide an interference fit. A cemented component may be inserted into holes having a less demanding tolerance, and which allow space for a cement mantle between the peg and the bone.

Figure 8:
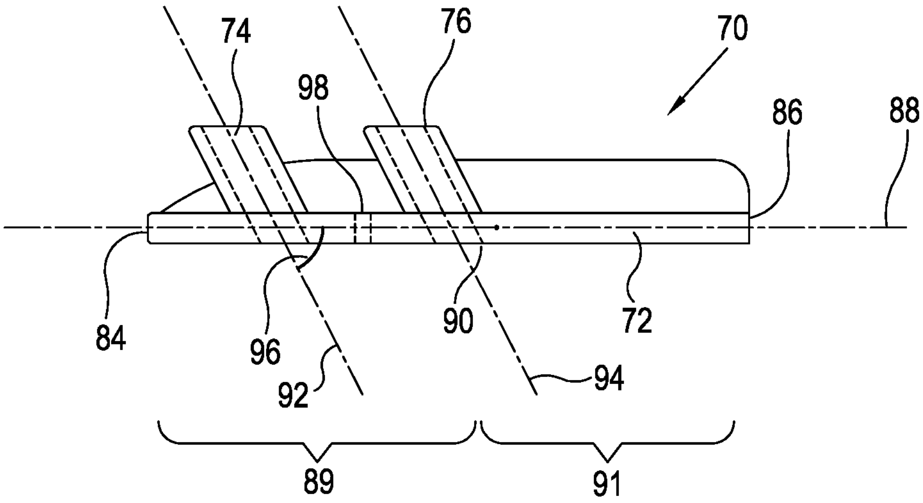
FIG. 8 shows a drill guide for use in a method of implantation.

Nevertheless, drilling oblique parallel holes in a surgical procedure is not a straightforward matter, and to assist in the installation process a surgeon may find assistance by means of a guide tool 70 of the type shown in FIG. 8.

The guide tool 70 has a guide plate 72, and at least one drill guide, in this case first and second drill guides 74 and 76.

The guide plate 72 is shaped to replicate a plate of a tibial component that is to be installed, such as the plate 12 of the tibial component 10 described above. To that end, the guide plate 72 is, in the example shown, substantially flat, and has an outline shaped to mimic the natural shape of the head of a patient's tibia. The example shown is a guide plate for a medial tibial component, and hence the plate is generally C-shaped on a medial side, and comprises an upstanding lip on an opposing lateral side.

The guide plate 72 has an anterior end 84, a posterior end 86, and medial side and a lateral side. A mediolateral width of the plate is defined between the medial and lateral sides, and a longitudinal anteroposterior axis 88 extends between the anterior and posterior ends approximately one third of the width of the guide plate from the lateral side, and defines a longitudinal axis length of the guide plate.

A hypothetical line 90 extending mediolaterally across the guide plate divides the guide plate mediolaterally into an anterior portion 89 and a posterior portion 91. In the example shown, the anterior portion comprises a part of the guide plate defined by an anterior 50% of the longitudinal axis length (also termed herein the anterior 50% of the guide plate), whilst the posterior portion comprises a part of the guide plate that is defined by a posterior 50% of the longitudinal axis length (i.e. the remainder of the guide plate, also termed herein the posterior 50% of the plate).

The first drill guide 74 is configured to guide a drill through the guide plate 72 along a first drill axis 92. The second drill guide 76 is configured to guide a drill through the guide plate 72 along a second drill axis 94. The first and second drill axes 92, 94 are substantially parallel to one another and are disposed at an angle 96 with respect to the longitudinal anteroposterior axis. The angle may be between 45-70 degrees, for example between 55-65 degrees, and in the example shown is around 60 degrees.

The drill guides 74, 76 may be provided in form of hollow tubes, such as cylinders, through which a surgical drill bit can be passed. The diameter of the hollow within the respective cylinders may be the same as or narrower than diameter of the pegs on the component to be fitted (e.g. 0.5 mm, or 1 mm narrower).

In the example shown the guide plate comprises an anteroposterior length, defined as discussed above with respect to the longitudinal axis 88, the first drill guide 74 being located one fifth of the length of the guide plate 72 and the second drill guide 76 being located half of the length of the guide plate.

Such a guide tool 70 may be used to drill a pair of parallel angled holes into which the elongate pegs 14, 16 of a tibial component of the type described herein may be fitted. It will be appreciated that the drill guides could be spaced differently, if required, and/or angled differently—the spacing and angle of the drill guides should match the spacing and angle of the pegs on the component to be fitted.

The guide tool may also include a hole 98 through the guide plate, which in the example shown is located between and medial of the first and second drill guides.

Figure 9:
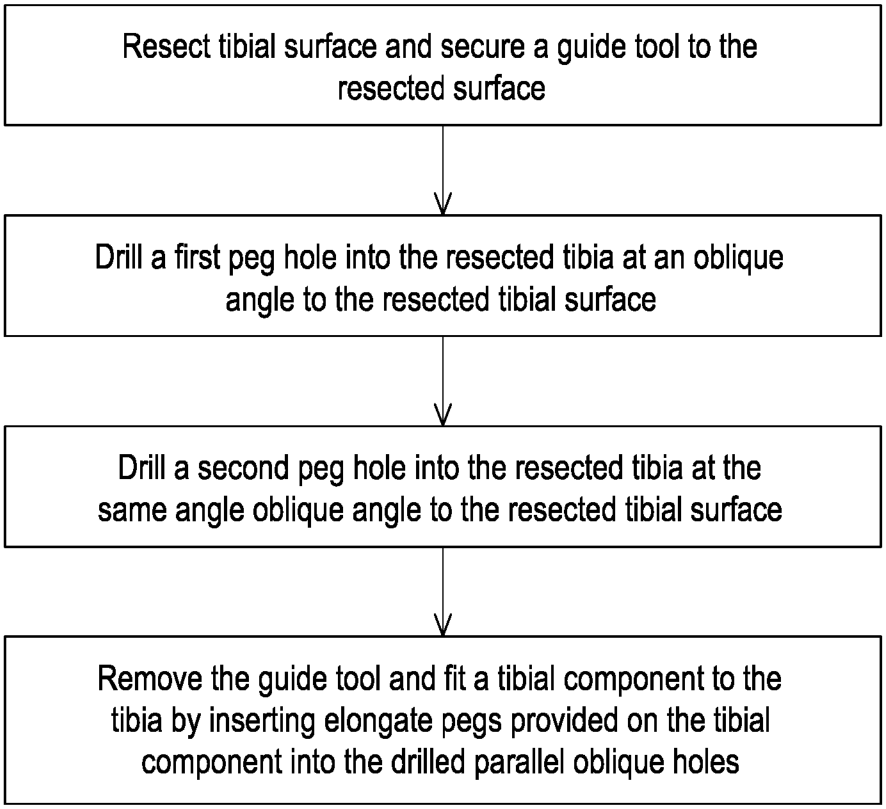
FIG. 9 depicts a method of implantation.

An exemplary method installation will now be described, with reference to FIGS. 9, 10 and 11. As an initial step, a surface of a patient's tibia that is to be replaced is resected and prepared to receive an implant (or trial implant). A guide tool 70 is then placed on the resected surface and secured in place.

The guide tool may be secured by means of a pin 100 or other suitable temporary fixation member that is passed through the hole 98. A clamp (schematically illustrated at 102) may also be provided to engage between the patient's femur 104 and a posterior of the guide plate 72. Such a clamp could be attached the top surface at the back of the guide plate. The clamp would be adjusted so it is pushing up on the surface of the femoral condyle above thus pushing the guide tool 70 firmly down onto the tibia.

Figure 10:
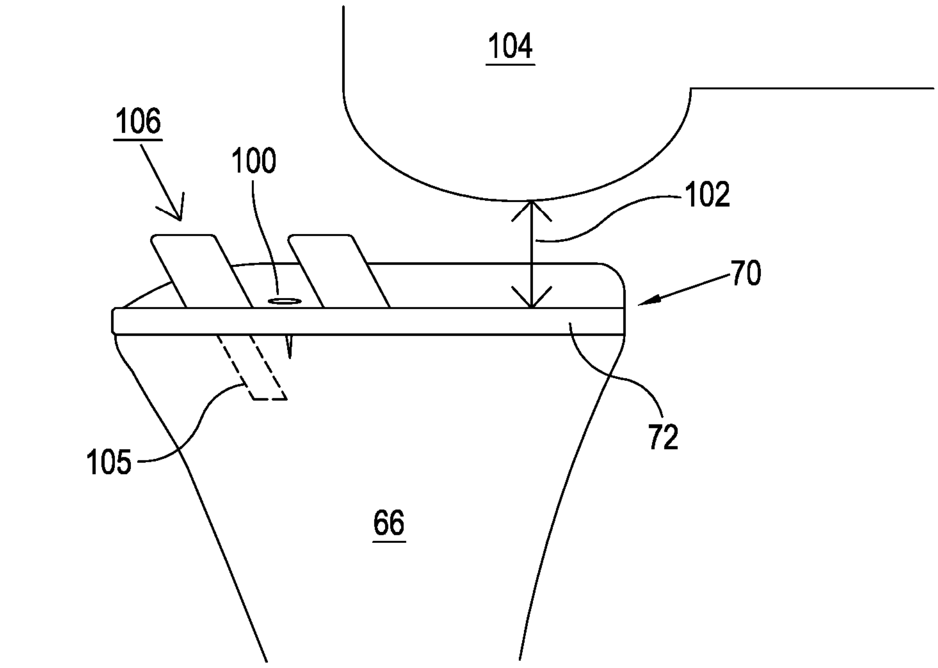
FIG. 10 schematically illustrates use of the drill guide of FIG. 8 in a method step of FIG. 9.

As shown in FIG. 10, once the guide tool has been secured to the resected tibial surface, an anterior implant hole 105 is drilled into the resected tibia at an angle that is oblique to the resected tibial surface, schematically illustrated by arrow 106.

Figure 11:
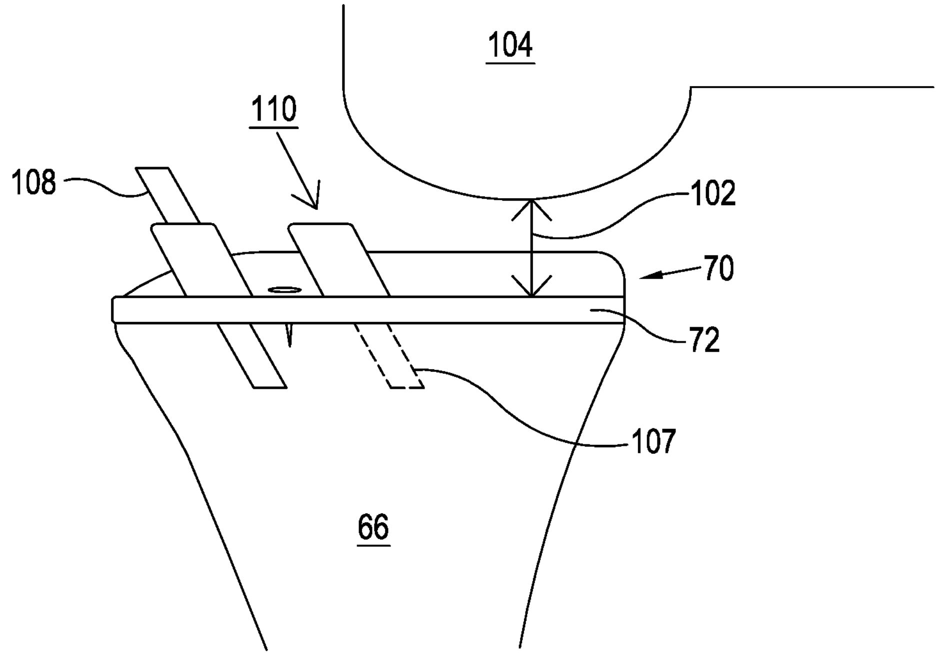
FIG. 11 schematically illustrates use of the drill guide of FIG. 8 in a subsequent method step of FIG. 9.

As shown in FIG. 11, a stabilising rod 108 is then inserted into the drilled anterior hole to stabilise the guide tool. A second hole 107 is then drilled into the resected tibia at an angle that is oblique to the resected tibial surface, schematically illustrated by arrow 110.

The two drilled holes are parallel to one another and are both at the same oblique angle to the resected tibial surface.

A drill, indicated schematically by arrows 106, 110, may be used by a surgeon to drill the first and second holes. Such a drill may comprise a drill stop operable to impact a corresponding drill stop on a surface of the guide tool (e.g. on the guide plate and/or drill guide) when a hole has been drilled to a specified depth (e.g. 6, 7, 8, 9, 10, 11 or 12 mm), to prevent the surgeon from inadvertently drilling too deeply. Such a drill could have a tapered drill bit if it required to drill a tapered hole.

A tibial component of the type described above (i.e. having a pair of parallel and obliquely angled elongate fixation pegs) may then be fitted into the drilled holes. The holes may be drilled to be slightly narrower than the pegs of the implant component, so as to promote an interference fit.

Tibial components of the type discussed herein may reduce the likelihood of posterior tibial collapse and/or fracture following a tibial resurfacing procedure. The oblique nature of the pegs resists the component lifting anteriorly after installation. It will be appreciated that any number of pegs may be provided, e.g. 1, 2, 3, 4 or 5 pegs.

If more than one peg is provided all the pegs must be parallel for a cementless installation. The pegs may be located anywhere within the anterior portion of the component, although preferably not too close to the outer edge (in the example shown medial edge) of the plate. For instance, the pegs may be located anywhere that is more than a third of the width of the plate from the outer edge, for example more than half the width of the plate from the outer edge, e.g. between ½ and ⅘ of the width of the plate from the outer edge.

The lack of fixation pegs in a posterior part of the component means that the component can be installed with less damage to the posterior part of the patient's tibia. The absence of a keel or large diameter pegs reduces the risk of fracture further, and also reduces the risk of surgical errors such a making a vertical cut too deep or damaging the posterior cortex when making the keel slot.

The interference fit from keels or large diameter pegs in state of the art components can generate tension in the upper part of the resurfaced condyle, increasing the risk of fracture. In contrast the use of relatively narrow oblique pegs of the type described herein can provide fixation with minimal risk of fracture. With narrow (high aspect ratio/elliptical) pegs very little bone needs to be removed in the upper part of the tibia leaving a large amount to transmit tension and prevent fracture. In addition the pegs are a long way from the cortex.

Above we have discussed the benefits conferred by locating elongate fixation pegs in an anterior portion of a tibial component. We have found that a tibial component having a keel can also benefit from a more anterior placement of the keel. Siting the keel in a more anterior position as compared with current keels reduces the damage to the posterior part of the tibia (as discussed above). Further, a more anterior location reduces the need to work further back on the tibial platform. This can be difficult for a surgeon due using the newer minimally invasive techniques, which provide limited access to the posterior of the joint.

Figure 12:
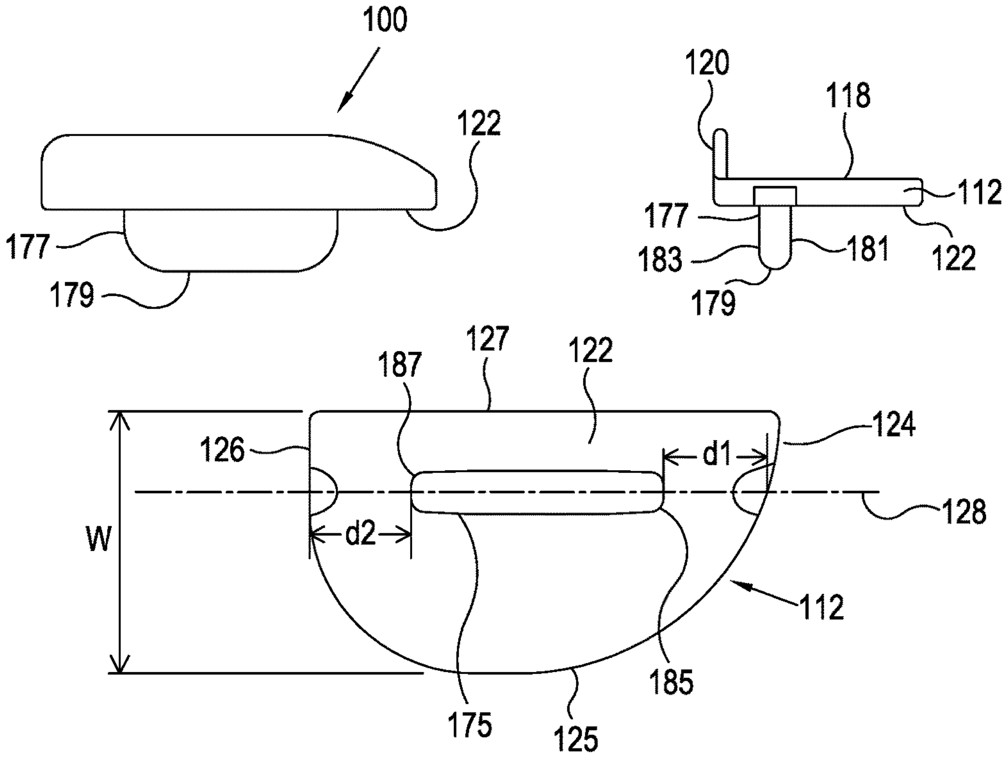
FIG. 12 shows, for purposes of comparison, a prior art size A tibial component having a centrally located keel.

For reference and comparison, FIG. 12 shows a prior art tibial component 100 in side elevation and front elevation (with bearing surface uppermost) and in plan view (with opposing surface uppermost). The component is a medial component in size A.

Like the components discussed above, the tibial component 100 includes a plate 112, configured to replace an articular surface of the patient's tibia, in this case a medial tibial bearing surface. The plate includes a bearing surface 118, which when installed will take the place of the patient's tibial bearing surface. The bearing surface 118 is thus shaped to cooperate either directly with a patient's femur (or a femoral replacement component) or with a bearing component located between the tibial component and the femur/femoral replacement component.

The plate 112 is, in the example shown, substantially flat, and has an outline shaped to mimic the natural shape of the head of a patient's tibia. The example shown is a medial tibial component, and hence the plate is generally C-shaped on a medial side, and comprises an upstanding wall or lip 120 on an opposing lateral side that is intended to abut a central tibial eminence of the patient's tibia, when the component is installed. A lateral tibial component would be a mirror image of the component that is shown. It will be appreciated that the plate could have a different shape, and may for instance be generally rounded or elliptical.

An opposing surface 122 of the plate is configured to be secured to a proximal end of a patient's tibia, as will be discussed in more detail later.

The plate 112 has an anterior end 124, a medial side 125, a posterior end 126 and a lateral side 127. A mediolateral width W of the plate is defined between the medial and lateral sides, and a longitudinal anteroposterior axis 128 extends between the anterior and posterior ends approximately one third of the width of the plate (i.e. ⅓W) from the lateral side, and defines a longitudinal axis length L of the plate.

Primary fixation is essential to hold the component still after implantation, so as to allow the bone to grow into and stick to the implant and achieve secondary fixation. To this end, the prior art tibial component shown includes a keel 175 projecting from the opposing surface. The keel 175 is an elongate projection having a length in an anteroposterior direction that is greater than its width in a mediolateral direction. The keel projects distally from the opposing surface, in this example substantially perpendicular to the opposing surface (although this need not be the case). The keel comprises a base 177 adjacent to the opposing surface and a tip 179 distal from the base. The keel also includes a medial wall 181 and a lateral wall 183.

The keel 175 of the prior art component shown in FIG. 12 is located centrally on the opposing surface. "Centrally" in this instance means centrally with regards to the anteroposterior axis 128. In particular, the keel is spaced such that a distance d1 between a leading edge 185 of the keel and the anterior end 124 of the plate is approximately the same as a distance d2 between a trailing edge 187 of the keel and the posterior end 126 of the plate. The keel is not located centrally with respect to the width W of the plate—rather, it is located approximately ⅓W from the lateral side, similarly to the pegs discussed above.

Figure 13:
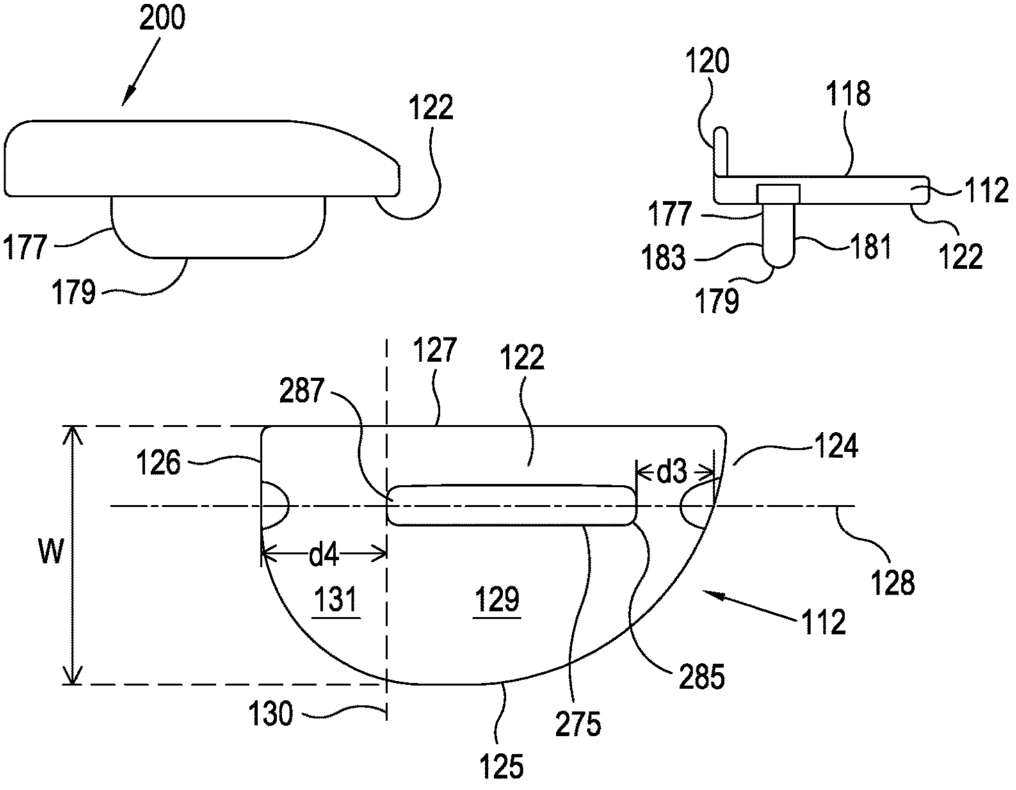
FIG. 13 shows a size A tibial component having an anterior keel.

Typical dimensions for a plate having a central keel of the type shown in FIG. 12 are as follows:

AP axis length L=44.92 mm keel length=25.92 mm d1=d2=9.50 mm keel distance from lateral side=⅓W=7.98 mm In contrast, an alternative unicompartmental tibial component 200 is shown in FIG. 13. Like reference numerals are used for like components, and those components will not be discussed again in the interest of brevity.

Unlike the component shown in FIG. 12, the component 200 includes a keel 275 that is not located centrally. That is, a distance d3 between a leading (anterior) edge 285 of the keel and the anterior end 124 of the plate is different to, and in particular less than, a distance d4 between a trailing (posterior) edge 287 of the keel and the posterior end 126 of the plate. The keel 275 is, in this example, the same length as the prior art keel 175; however it is located closer to an anterior rim of the plate than to the posterior rim. As before, the keel is not located centrally with respect to the width W of the plate—rather, it is located approximately ⅓W from the lateral side, similarly to the pegs discussed above.

Example dimensions for a plate having an anterior keel of the type shown in FIG. 13 are as follows:

AP axis length L=44.92 mm keel length=25.92 mm d3=7.94 mm d4=11.08 mm keel distance from lateral side=⅓W=7.98 mm It can thus be seen that the keel of component 200 is located approximately 1.5 mm further forward than in the case of a prior art keel. However, the keel may be located further anteriorly if required.

The distance d3 may be between 50-85% of the distance d4, for example 60%, 65%, 70%, 75% 10 or 80%.

To this end it is useful to consider the plate 112 as comprising a hypothetical line 130 dividing the plate medio-laterally into an anterior portion 129 and a posterior portion 131. In the example shown, the anterior portion comprises a part of the plate defined by an anterior 76% of the longitudinal axis length L (also termed herein the anterior 76% of the plate), whilst the posterior portion comprises a part of the plate that is defined by a posterior 24% of the longitudinal axis length L (i.e. the remainder of the plate, also termed herein the posterior 24% of the plate).

It will be appreciated that the dividing line 130 may divide the longitudinal axis differently, for example, the anterior portion could be defined as the anterior 70% of the plate, with the posterior part then being the remaining (posterior) 30% of the plate. The anterior:posterior ratio between the anterior part of the plate and the posterior part of the plate may be 77:23 or less, e.g. 70:30, 65:35, 60:40, 55:45 or 50:50. The posterior portion thus comprises at least 23% of the plate, as defined according to the longitudinal axis length, as discussed above, and preferably 24%, 25%, 26%, 27%, 28%, 29% or more.

Figure 14:
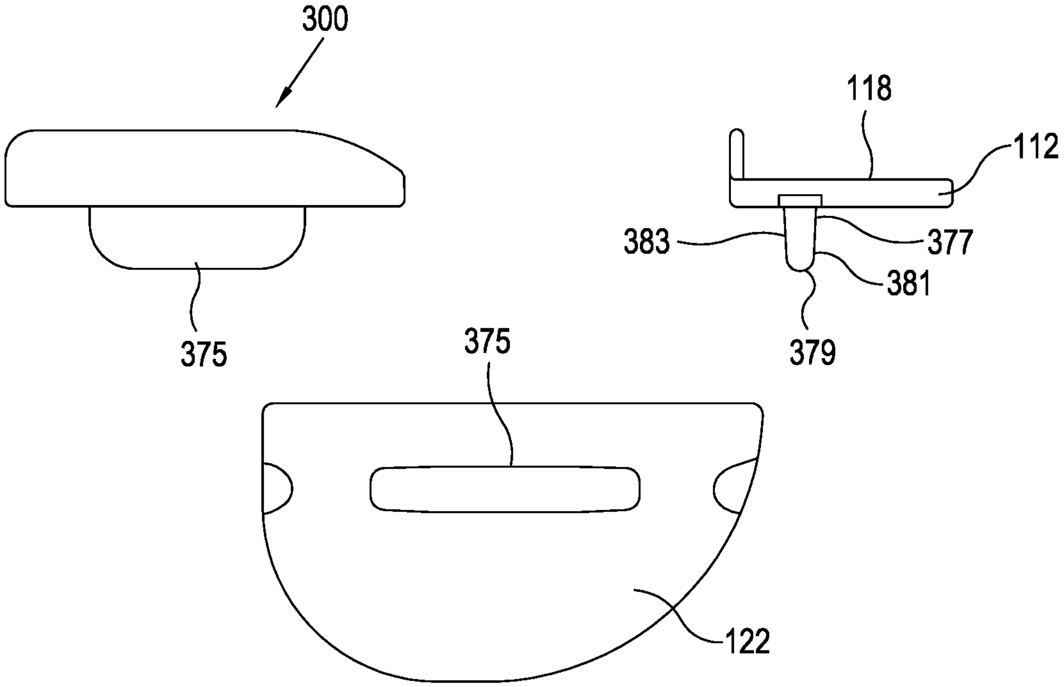
FIG. 14 shows a size A tibial component having a tapered central keel.
Figure 15:
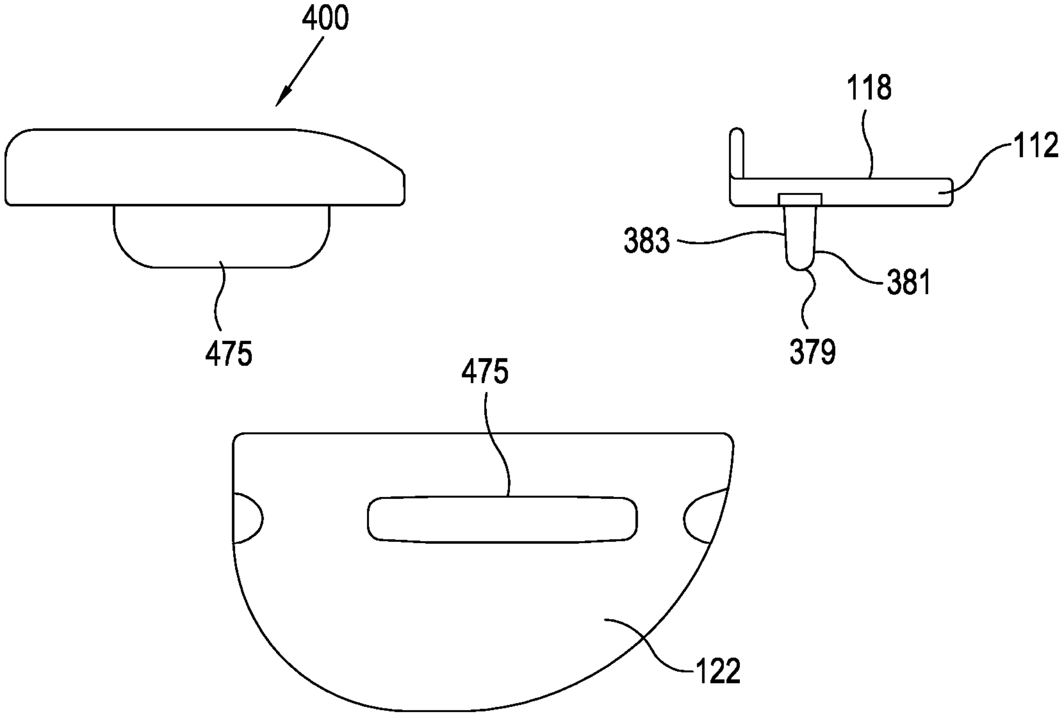
FIG. 15 shows a size A tibial component having a tapered anterior keel.

FIGS. 14 and 15 show tibial components 300, 400 similar to those of FIGS. 12 and 13, except that the keels 375, 475 of those components are tapered. As used herein "tapered" means that the medial and lateral side walls 381, 383 taper inwardly from the base portion 377 towards the tip 379. That is, the keel is narrower in width (i.e. thinner) towards the tip than it is at the base portion which adjoins the opposing surface. Such a tapering keel allows for a tighter interference fit into the tibia, reducing the likelihood of loosening over time.

The taper angle may be between 0.5-4 degrees, for example 1, 2 or 3 degrees. In an example where the keel protrudes from the plate in an orientation that is perpendicular to the opposing surface, the taper angle may be measured with respect to a plane perpendicular to the opposing surface.

Figure 16:
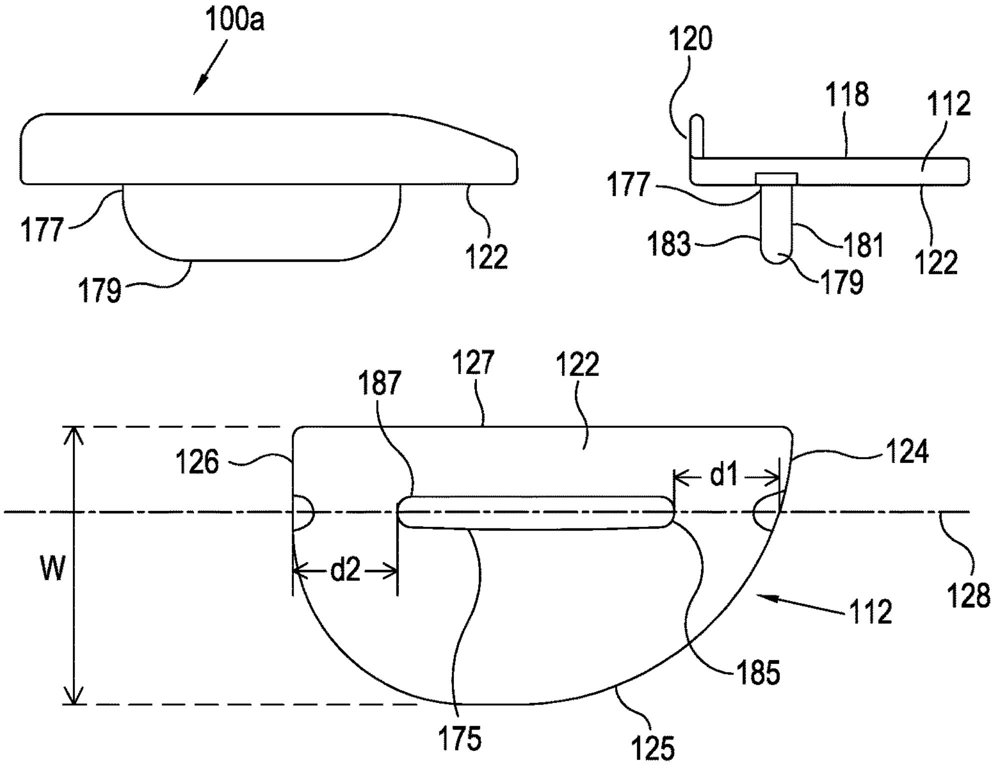
FIG. 16 shows, for purposes of comparison, a prior art size G tibial component having a centrally located keel.
Figure 17:
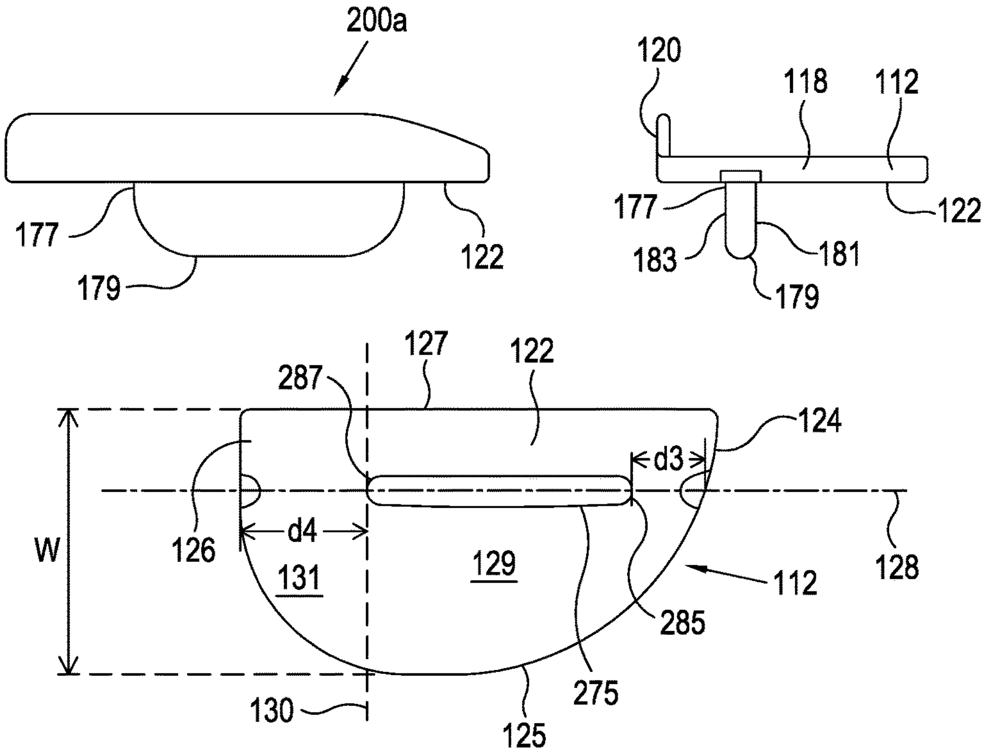
FIG. 17 shows a size G tibial component having an anterior keel.
Figure 18:
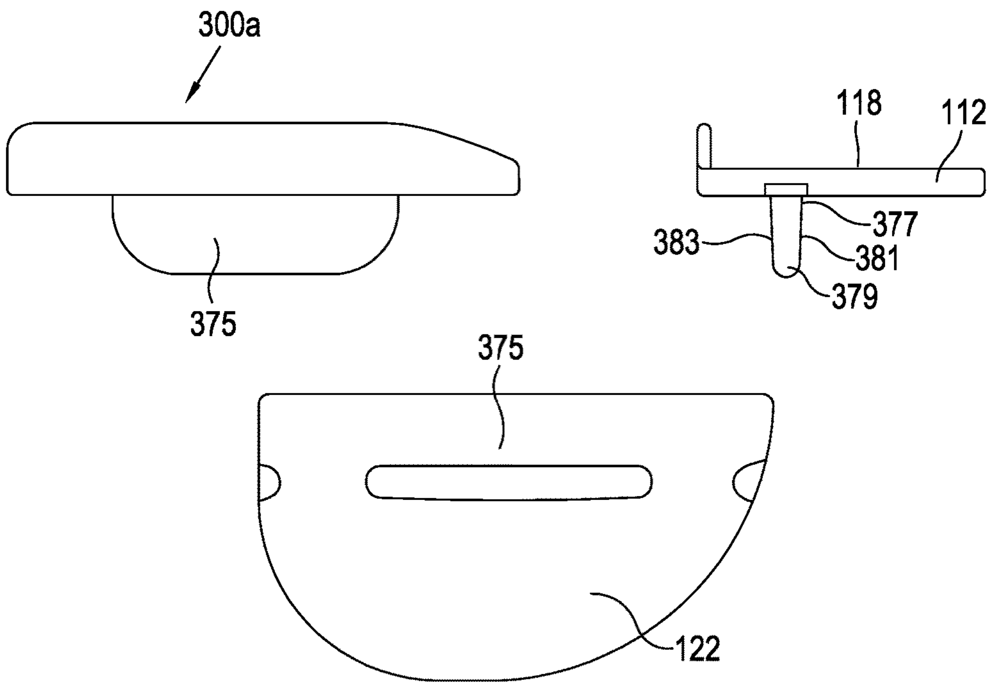
FIG. 18 shows a size G tibial component having a tapered central keel.
Figure 19:
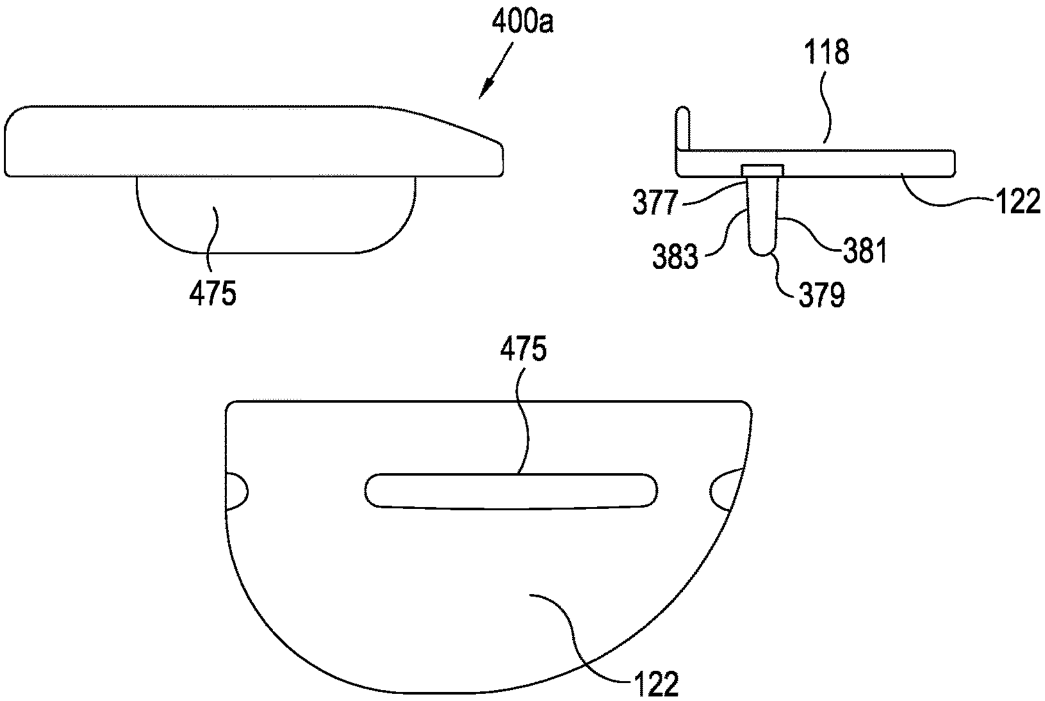
FIG. 19 shows a size G tibial component having a tapered anterior keel.

FIG. 16 shows a prior art tibial component 100*a* similar to the component of FIG. 12, with the exception that the component in FIG. 16 is in size G. Similarly, FIGS. 17-19 show size G components 200*a*, 300*a* and 400*a* similar to the size A components shown in FIGS. 13-15. Like reference numerals are used for brevity, and it should be understood that the description above of FIGS. 12-15 applies equally to FIGS. 16-19.

The sides of the keels shown in any of FIGS. 12-19 may comprise a surface to encourage boney ingrowth, such as a porous or microporous coating, of the type discussed above.

However, we have realised that, even in a cementless component, it can be preferable to leave some or all of the surfaces of the keel smooth.

When a keel is implanted into a patient's tibia, typically a keel slot is cut into a prepared surface of the tibia. The keel of a tibial component is then inserted posteriorly and downwardly into the slot at an angle and, when the keel reaches the most posterior extremity of the slot, the tibial component is rotated to a level position and pushed downwardly into the slot. We have noticed that keels with rough surfaces, designed for boney ingrowth, can act as a rasp going in and widen the prepared keel slot, which can result in a poor fit or loosening over time.

Thus, the sides of the keels shown in any of FIGS. 12-19 may be smooth. That is, the outer surfaces of the keels may be free from any rough surfaces designed to encourage boney ingrowth, such as a porous or microporous coating. There is limited need for boney ingrowth on the sides of the keel as sufficient can be obtained on the underside of the tibial platform. Making the sides of the keel smooth avoids the above-described rasp-like effect, and can result in an improved component fit.

Figure 20:
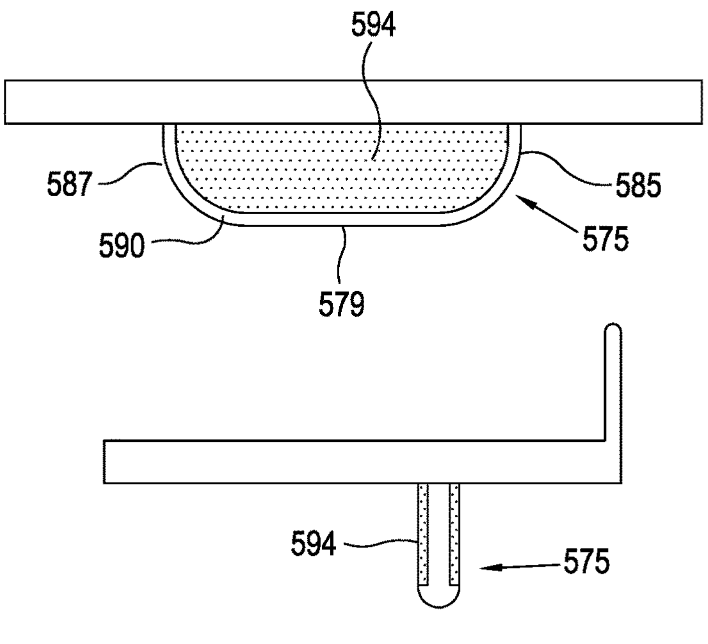
FIG. 20 schematically illustrates a tibial component including a keel having a smooth outer rim.
Figure 21:
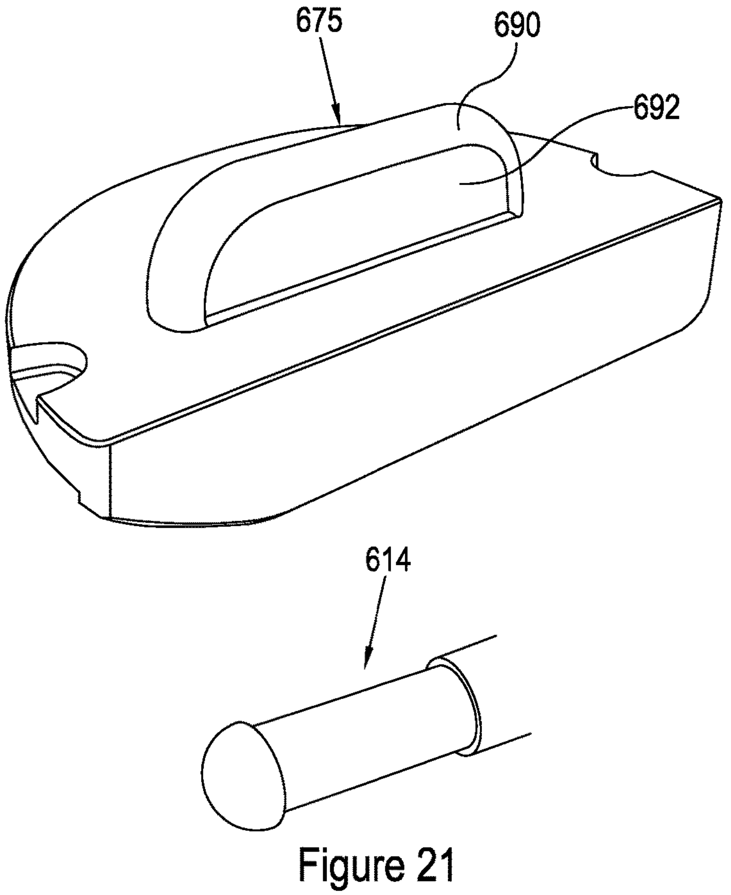
FIG. 21 illustrates a keel similar to that shown in FIG. 20, and also a peg.

FIGS. 20 and 21 illustrate alternative example keels 575, 675 which have a smooth insertion surface. "Insertion surface" refers herein to a surface of a fixation feature operable to be inserted into a boney cavity first, thus leading the way for the remainder of the fixation feature. The rasp effect of such an insertion surface, if rough, would be significantly higher than any rasp effect due to the remainder of the fixation feature. Thus providing a smooth insertion surface significantly reduces the rasp effect mentioned above. The remainder of the fixation feature may be provided with an (uncoated) surface structure or treatment which encourages bone ingrowth so as to still maintain a large coated surface area for boney ingrowth.

In particular, the keels shown in FIGS. 20 and 21 include a smooth outer rim 590, 690. The smooth outer rim includes at least a portion of a posterior (trailing) edge 587 of the keel, as well as at least a portion of the distal edge 579. In the specific example shown in FIGS. 20 and 21, the outer rim includes substantially the entire posterior edge 587 and distal edge 579, as well as some or all of an anterior (leading) edge 585.

The remaining surfaces of the keel (i.e. surfaces other than the smooth insertion surfaces) can be provided with a cementless coating in order to improve secondary fixation. For example, in the illustrated examples, a pocket 692 is defined by the outer rim. The pocket has a depth that is similar to or greater than a thickness of a porous or microporous coating 594, so that such a coating can be received in the pocket and be substantially flush with or below the smooth outer surface of the outer rim. The depth may be, for example, 0.35-0.4 mm or greater.

Having a well-positioned and tight keel helps with cementless fixation as it holds the implant in place until boney ingrowth develops. An extension of the smooth or partially smooth sided keel would be to have a keel with rough or partially rough sides for ingrowth but covered with a bioabsorbable substance such as a calcium paste. The bioabsorbable substance would thus provide a smooth insertion surface that will be absorbed over time, so as to encourage growth into the rough cementless fixation surface if there is a need for larger bone attachment surfaces.

It will be appreciated that other fixation features, such as pegs of the types discussed above and more conventional non-oblique or non-anterior pegs. may also benefit from smooth sides and/or smooth insertion surfaces. A peg 614 including a smooth insertion region and a pocket is shown in FIG. 21. The insertion region is in the example shown a tip of the peg. The tip is rounded, and in particular part-spherical, to further assist with insertion.

It should be noted that in any of the exemplary aspects discussed above, smaller sized implants could have a reduced plate thickness in comparison to the larger sized implants to minimise bone removal and/or smaller sized implants could have reduced keel (or peg) depths as compared with larger sized implants to minimise tibial fracture, as discussed in our earlier patent publication US2013/0166073, the contents of which are hereby incorporated by reference.

It will be appreciated by one skilled in the art that changes may be made to the examples described above within the scope of the claims set out below. Features from different examples are combinable together. It is thus to be understood that the invention is not limited to the examples described above but is instead defined by the scope of the claims.

The invention claimed is:

1. A unicompartmental tibial component comprising:

a plate having a bearing surface and an opposing surface that is configured to be secured to a proximal end of a patient's tibia, wherein the plate further comprises an anterior end, an outer side, a posterior end and an inner side, wherein a mediolateral width (W) of the plate is defined between the outer and inner sides, and a longitudinal anteroposterior axis extends between the anterior and posterior ends approximately one third of the width of the plate (⅓W) from the lateral side, and defines a longitudinal axis length (L) of the plate;

a first elongate peg protruding from the opposing surface in the anterior portion, the first elongate peg defining a first peg axis; and a second elongate peg protruding from the opposing surface in the anterior portion, the second elongate peg defining a second peg axis;

wherein the first and second peg axes are disposed at an angle of 45-70 degrees with respect to the longitudinal anteroposterior axis and are substantially parallel to one another such that the first and second pegs protrude posteriorly as well as distally with respect to the plate;

wherein an anterior portion of the plate comprises a part of the plate defined by an anterior 60% or less of the longitudinal axis length (L), whilst a posterior portion of the plate comprises a part of the plate that is defined by the remaining posterior 40% or more of the longitudinal axis length (L), the posterior portion of the opposing surface being free from pegs or other fixation devices;

wherein the first and second elongate pegs are located more than half of the mediolateral width (W) of the plate from an outer edge of the plate; and wherein the component is configured for cementless fixation using an interference fit.

2. The unicompartmental tibial component of claim 1, wherein the first and second peg axes are disposed at an angle of approximately 60 degrees with respect to the longitudinal anteroposterior axis.

3. The unicompartmental tibial component of claim 1, wherein one or more of the elongate pegs has a high aspect ratio; each peg having a length of 6-12 mm and a widest diameter of 4-8 mm.

4. The unicompartmental tibial component of claim 1, wherein:

(i) a cross section of one or more of the elongate pegs is elliptical; or (ii) one or more of the elongate pegs is tapered.

5. The unicompartmental tibial component of claim 1, wherein one or more of the elongate pegs comprises a rounded or tapered tip.

6. The unicompartmental tibial component of claim 1, the first elongate peg being located one fifth of the anteroposterior axis length and the second elongate peg being located half of the anteroposterior axis length.

7. The unicompartmental tibial component of claim 1, wherein one or more of the elongate pegs comprises one or more barbs.

8. The unicompartmental tibial component of claim 1, wherein the component comprises a cementless fixation coating on each of the elongate pegs; wherein the coating is absent from a region of each peg, such that each said region has a diameter that is narrower than a widest diameter of the coated peg.

9. The unicompartmental tibial component of claim 8, wherein the coating is absent from a base region of each peg adjacent the opposing surface, such that each said base region has a diameter that is narrower than a widest diameter of the coated peg.

10. The unicompartmental tibial component of claim 1, wherein one or more of the elongate pegs comprises a region which is narrower than a widest diameter of the peg.

11. The unicompartmental tibial component of claim 1, wherein the component comprises a cementless fixation surface and/or coating on the opposing surface, and wherein the first and second elongate pegs comprise a cementless fixation surface and/or coating which is partially or completely covered with a smooth bio-absorbable coating.

* * * * *